United States Patent
Reid et al.

(10) Patent No.: US 10,004,823 B2
(45) Date of Patent: Jun. 26, 2018

(54) METHOD AND SYSTEM TO DETECT THAT A DEVICE HAS BEEN CLEANED

(75) Inventors: W. Scott Reid, Derry, NH (US); Brian D. Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1290 days.

(21) Appl. No.: 13/384,348

(22) PCT Filed: Jun. 15, 2010

(86) PCT No.: PCT/IB2010/052691
§ 371 (c)(1),
(2), (4) Date: Jan. 17, 2012

(87) PCT Pub. No.: WO2011/010233
PCT Pub. Date: Jan. 27, 2011

(65) Prior Publication Data
US 2012/0116803 A1    May 10, 2012

Related U.S. Application Data (60) Provisional application No. 61/227,858, filed on Jul. 23, 2009.

(51) Int. Cl.
*G06Q 50/22* (2018.01)
*G06Q 10/06* (2012.01)
*A61L 2/28* (2006.01)
*G16H 40/20* (2018.01)

(52) U.S. Cl.
CPC ............ *A61L 2/28* (2013.01); *G06Q 50/22* (2013.01); *G16H 40/20* (2018.01)

(58) Field of Classification Search
None
See application file for complete search history.

(56) References Cited

U.S. PATENT DOCUMENTS

| | | | | |
|---|---|---|---|---|
| 5,869,007 | A * | 2/1999 | Jang | 422/82.02 |
| 6,647,765 | B2 * | 11/2003 | Downing | 73/104 |
| 7,467,629 | B2 | 12/2008 | Rand | |
| 9,069,390 | B2 * | 6/2015 | Marsden | G06F 3/023 |
| 2003/0074222 | A1 * | 4/2003 | Rosow et al. | 705/2 |
| 2004/0138925 | A1 | 7/2004 | Zheng | |
| 2007/0055698 | A1 * | 3/2007 | McCoy | G06Q 50/08 |
| 2007/0210917 | A1 | 9/2007 | Collins, Jr. et al. | |
| 2009/0276239 | A1 * | 11/2009 | Swart et al. | 705/2 |

FOREIGN PATENT DOCUMENTS

| | | | |
|---|---|---|---|
| EP | 0341022 | A2 | 11/1989 |
| EP | 1623666 | A2 | 2/2006 |
| EP | 1845315 | A2 | 10/2007 |
| JP | 61122868 | | 6/1986 |
| JP | 3087419 | U | 9/1991 |

(Continued)

*Primary Examiner* — Michael Tomaszewski (57) ABSTRACT

A room monitoring system includes a plurality of in-room units. The in-room units collect information relating to a clean or dirty status of a plurality of patient rooms and/or equipment in the rooms. A monitoring station receives clean or dirty status information from the in-room units and determines which rooms are clean, and ready for a patient, which are dirty and in need of cleaning, and which are occupied.

17 Claims, 5 Drawing Sheets

(56) References Cited

FOREIGN PATENT DOCUMENTS

| | | | |
|---|---|---|---|
| JP | H0592860 | | 12/1993 |
| JP | 2001101267 | | 4/2001 |
| JP | 2003242230 | | 8/2003 |
| WO | WO 03/014871 | * | 8/2002 |
| WO | 03014871 A2 | | 2/2003 |
| WO | 2009033487 A1 | | 3/2009 |

* cited by examiner

METHOD AND SYSTEM TO DETECT THAT A DEVICE HAS BEEN CLEANED

CROSS REFERENCE TO RELATED APPLICATIONS

This application claims the benefit of U.S. provisional application Ser. No. 61/227,858 filed Jul. 23, 2009, which is incorporated herein by reference.

The present application relates to a network, system, or method for electronically determining whether rooms or equipment in a health care environment are clean or dirty. It finds particular application in improving and optimizing the workflow of cleaning rooms and placing patients in the clean rooms within a hospital environment and will be described with particular reference thereto. However, it will be appreciated that it is also applicable to nursing homes, clinics, other healthcare situations, hospitality facilities, and the like.

Presently, as the level of care of a patient changes, the patient is often held in a less than optimal unit within a hospital until a clean room in an appropriate unit becomes available. During this time, the resources of the hospital to provide a required standard of care are stressed. The hospital's ability to accept new patients is restricted while waiting for a bed to become available. After the patient is transferred to another unit, the vacated, used, or dirty room is effectively occupied or at least unavailable for new occupants until cleaned. Increasing the efficiency with which rooms are cleaned increases the number of available beds, hence patient throughput. Even when the room is cleaned, admitting may be slow to learn that the room is available for a new patient.

Room cleaning and indicating a room is clean is typically manually done. Many surfaces must be cleaned. As used herein, "cleaning" connotes removing dirt and bio load including washing, sanitizing, disinfecting, sterilizing, and other dirty or bio load removal techniques. If the cleaning personal forgets to clean or disinfect a surface it is often not visually apparent. Moreover, disinfecting surfaces typically requires contact with the disinfectant for a minimum duration. If the cleaning person cleans the surface too quickly or if the disinfectant has lost potency, a surface which is believed to be disinfected can actually carry an unacceptably high bio load. Currently, all medical devices need to be cleaned pursuant to the manufacturer's recommendations, however, in many cases, this is either not done or there is no way to determine if the end user is complying with the manufacturer's labeling. Additionally, even if all of the medical devices have been cleaned pursuant to the manufacturer's recommendations, only if the end user manually indicates that the medical equipment has been cleaned will admitting know that the room is clean and is available for a new patient.

The present application provides a new and improved system for optimizing the availability of rooms which overcomes the above-referenced problems and others.

In accordance with one aspect, a room monitoring system is provided. A plurality of in-room units collect information relating to a clean or dirty status of a plurality of patient rooms and/or equipment in the rooms. A room monitoring station receives clean or dirty status information from the in-room units and determines which rooms are clean, and ready for a patient, which are dirty and in need of cleaning, and which are occupied, and create transactions of clean/dirty based on Patient ID changes.

In accordance with another aspect, a method of displaying the status of one or more medical rooms is provided. Room status information is received from one or more sensors in each of the one or more medical rooms. A status is determined for each of the one or more medical rooms from the room status information received from the one or more sensors in each of the one or more medical rooms. The status of each of the one or more rooms is displayed in a display. A notification is generated for cleaning personal in response to determining one or more medical rooms has a dirty status.

In accordance with another aspect, a method is provided for verifying that the user has properly cleaned the equipment with the prescribed material and for the prescribed duration to ensure the equipment is adequately cleaned and does not destroy the equipment.

In accordance with another aspect, a method is provided for detecting the need for converting a dirty room or equipment to a clean room or equipment based on the equipment monitoring system's knowledge of which equipment is used for which patient by Patient ID and bed location.

One advantage resides in the improved assurance that rooms or equipment have been effectively cleaned and disinfected.

Another advantage resides in improved cleaning efficiency.

Another advantage resides in improved patient throughput.

Another advantage resides in the ability to track the clean/dirty state of portable devices (i.e. devices not kept in the room).

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
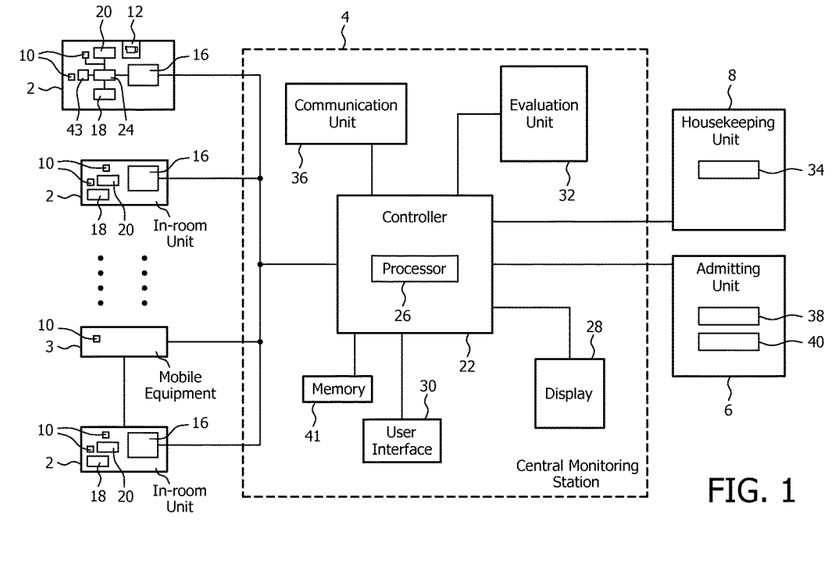
FIG. 1 is a diagrammatic illustration of a room monitoring system.

With reference to FIG. 1, a plurality of in-room units 2 collect current patient and cleaning information and communicate the clean/dirty information to a central station 4. The bed assigning unit 6 receives room status information from the central station 4, inputs and receives patient waiting information, and allows operator or automatically matching of waiting patients with available rooms. The central station 4 also communicates room status information, particularly dirty rooms in need of cleaning, to a housekeeping unit 8. A list of dirty rooms to be cleaned may be prioritized based on the needs of waiting patients. The central station 4 can be a separate unit as described below or may be combined with the bed assigning 6 or housekeeping 8 units.

Each room has one or more sensors 10 positioned in the room that measure cleanliness of medical equipment, patient beds, counters, other surfaces or the like and generate cleaning information indicative thereof to the corresponding in-room unit 2. In one embodiment, an electrochemical device senses the cleanliness of surfaces of rooms and medical equipment. The electrochemical device is affixed to or implanted in a surface of a room or piece of medical or healthcare equipment and senses whether the surface was subject to an appropriate cleaning chemical for an appropriate duration of time e.g. for surface disinfection. The electrochemical device sends this information along with the device or surface ID to the in-room unit 2 which, in turn, communicates information to the central monitoring station 4. The electrochemical device may also visually change colors or indicate symbology to notify cleaning or other personal that the surface is either clean or dirty.

In another embodiment, cameras 12, motion detectors, IR staff tracking systems, wireless in-building phone triangulation units, GPS units, and the like, are used to detect whether a room was properly cleaned. The cameras 12, motion detectors, wireless phone triangulation units, GPS units, and the like detect whether cleaning personal were present in a dirty room or in each part of the room for an appropriate amount of time to sufficiently clean the room. In one embodiment, the camera 12 may also be used to detect if a person wearing cleaning service attire was present in the room for a required amount of time to adequately clean the devices.

In another embodiment, the sensors 10 include a heterogeneous conductive matrix patch mounted between two electrode plates. Across these plates either the voltage or current can be modified such that a resulting resistance or impendence measurement can be made. The heterogeneous conduct matrix patch changes the capacitance and impedance of the matrix over a period of exposure to a disinfectant solution. In one embodiment, the system determines whether the proper cleaning/disinfecting solution was used. In another embodiment, the sensors 10 have a pressure output signal which is used for determining if the appropriate amount of force was applied to the device when rubbing with the cleaning fluid in contact with the device. For example, the system has logic to compare the cleaning solution signature, obtained with the comparative matrix to a stored reference signature in such a way that the system can determine if the correct cleaning solution was applied to the surface while also verifying the appropriate amount of pressure was applied during the scrubbing or wiping of the cleaning fluid. Once the sensor 10 detects an appropriate exposure to the prescribed cleaning fluid, with the appropriate force for the appropriate amount of time, the sensor sends an electronic signal to the processor 24 or the central monitoring station where the decision to declare the device clean is made by comparing the cleaning solution spectrum and applied pressure to the manufacturer's recommendation stored in the local memory of the in-room unit 43 or the central station 41 (not shown).

A camera may also be embodied to detect the cleanliness of a room. The camera 12 takes current pictures of a room's medical equipment, beds, and the like and compares the pictures are compared in the in-room unit 2 or the central station 4 to pictures of the same medical equipment, beds, and the like in a clean or made-up state to determine if the medical equipment is clean or dirty. In another embodiment, the camera 12 images the electrochemical device whose appearance (e.g. color or symbology) changes to indicate a clean or dirty status. In another embodiment, the electrochemical device has an IR output that is seen by the camera 12. When the electrochemical device senses the equipment is dirty, the cleaning personal is summoned.

In another embodiment, the sensors 10 can also generate cleaning information based on mobile medical equipment that is not permanently assigned to a particular room. In one embodiment, a mobile medical equipment 3 unit collects cleaning information from one or more sensors 10 attached to a piece of mobile medical equipment. The mobile medical equipment unit 3 communicates the cleaning information to the central monitoring station 4 or the in-room unit 2. The sensors 10 may include RF tracking units that track changes in the medical equipment ID, or patient ID as it is moved in and out of the room or throughout the hospital. Through the use of RF tracking, the sensors 10 track if a piece of mobile medical equipment is removed from the room during cleaning and a different piece of the equipment is brought in. In another embodiment, the sensors 10 of the mobile medical generate cleaning information based on the assignment of a patient ID to the mobile medical equipment. In another embodiment, the equipment is tracked to be sure that the different piece has come directly to the room from a sterilization unit or housekeeping thereby indicating the medical equipment brought into the room is actually clean. Sensors in other parts of the health care facility can also track the mobile medical equipment recently left a room to be sure that it goes to the sterilization unit or housekeeping without being reused. The tracking determines whether equipment assigned to a room is clean or dirty. In another embodiment, the sensors 10 include a colorometric indicator on the mobile medical equipment whose color is changed when used (or cleaned) to indicate whether the surface of the item is dirty (or cleaned). The color can be checked manually or with the camera 12. In another embodiment, the sensors 10 include a wireless electrochemical device or heterogeneous conductive matrix patch as described above. Of course, other sensors 10 can be associated with the mobile medical equipment, and not all of the above-mentioned sensors 10 have to be associated with the mobile medical equipment at any given time.

In another embodiment, the sensors 10 generate cleaning information based on the assignment of the medical equipment to a patient ID or change of assignment of the medical equipment to different patient IDs. For example, in the case where the in-room unit 2 or medical equipment is a patient monitor or device which stores the ID of a patient with whom it is associated, the sensors 10 can generate information indicative of the assignment of a patient ID to the medical equipment. The patient ID can automatically be assigned to in-room unit 2 or the medical equipment by the bed assigning unit 6 or central monitoring station 4, manually inputted by medical personal at the in-room unit 6 or medical equipment, automatically assigned by other medical equipment associated with the room or patient, or the like. In another embodiment, the sensors 10 generate cleaning information based on the change of a patient ID assigned to the in-room unit 6 or the medical equipment, reception of vital signals from the in-room unit 6 or the medical equipment, the detection of the patient ID assigned to the in-room unit 6 or the medical equipment being assigned to a different in-room unit 6 or the medical equipment, or the like.

As another example, when a clean piece of equipment is brought into a room, the ID of the patient in the room automatically is associated with it. If the equipment not clean or assigned to another patient ID, a warning is generated. Conversely, when a patient enters a clean room one of the sensors 10 reads the patient ID or the ID of the assigned patient is received from the central unit and that patient ID is assigned to all the equipment in the room. Once the ID is assigned to a piece of equipment that piece of equipment is usable only by the patient with the assigned ID. To all other patients, the equipment is dirty and any attempts by other patients to use it will results in a dirty warning.

The sensors 10 within the room report the cleaning information to a local buffer 16 of the in-room unit 2. The buffer 16 serves as a gathering point for the cleaning and patient ID information measured by the sensors 10 of the room and provides temporary storage for the data. The in-room unit 2 in one embodiment is a permanent fixture, such as a wall-mounted monitor that is permanently associated with each room. The communication links between the sensors 10 and the local buffer 16 may be wireless, hard wired, or a combination of both. Similarly, the sensors 10 may be powered by solar, battery, receive power from the host device, external AC power, or a combination of both.

The local buffers 16 communicate with the central monitoring station 4. The processor 24 can determine clean/dirty status. Alternatively, raw cleaning information can be communicated continuously, periodically when polled, or the like and the clean/dirty determination made at the central station. Some sensors 10 may communicate data continuously, such as electrochemical device, and other sensors 10 may include a trigger, such as an accelerometer to detect mechanical rubbing, to initiate a measurement and communication of the cleaning information. The communications links between the buffers 16 and the central monitoring station 4 may be wireless, hard wired, or a combination of both. If the buffer 16 is embodied in a more permanent fixture, the communications links between the buffers 16 and the central monitoring station 4 may be hard lines, such as standard Ethernet network cables.

The in-room unit 2 also includes a user interface or display 18 that allows the user to view and/or manipulate the data displayed on the display 18. An input 20 can be a separate component or integrated into a display 18 such as with a touch screen monitor. In one embodiment, the clean/dirty status of each piece of medical equipment, area of a room, the room itself, or the like can be inputted manually through the use of the user input 20. In another embodiment, the status of a room can be input manually through the use of a switch or physical signaling device within the room. Of course, other manual input devices 20 can be associated with the room, and not all of the above-mentioned manual input devices 20 have to be associated with the room at any given time. In another embodiment, the in-room unit 2 is a PDA, PC, tablet PC, and the like.

The interface display 18 can also display a check list of chores to be performed pursuant to a room cleaning protocol. The cleaning person can check-off, e.g. with a touch screen 18, each chore as it is performed. If a sensor 10 verifies any of the chores, the display 18 can indicate that the chore was not satisfactorily performed, e.g. "surface not completely disinfected." In one embodiment, the in-room unit 2 also includes a processor or controller 24 to evaluate the cleaning information received from the sensors 10 and the input 20 to determine the status of the room. The processor or controller 24 can also control the buffer 16, the display 18, the input 20, the communications with the central station, and the like.

At the central station 4, a controller 22 receives the cleaning information from the buffers 16 of the rooms for which the central monitoring station 4 is responsible. The central station controller 22 evaluates the cleaning information received from the in room-units 2 and determines a status of each room. In one embodiment, the in-room unit 2 also includes a processor or controller 24 to evaluate the cleaning information received from the sensors 10 and the input 20 to determine the status of the room. When a patient leaves a room, the removal of that patient's ID from the room automatically causes all equipment in the room to be marked dirty. The statuses given to a room include a dirty status, a clean status, a cleaning in progress status, an occupied or assigned status, and the like. A room given a dirty status describes a room in need of cleaning. Although some of the medical equipment may be cleaned; a dirty status is still assigned if the room or equipment is not completely clean, still contains contamination, was not suitably disinfected, was not cleaned to predefined standards or to a manufacture's recommendation, or the like. A clean status is assigned to a room that is ready for a new patient, that is, all the medical equipment and the room are clean and sanitized. The status of cleaning in progress indicates that the room is currently being cleaned by cleaning personal. A room is assigned an occupied status when a patient is assigned to or currently occupies the room. The controller 22 may include a suitable programmed computer or processor 26, software applied by the processor 26, or the like. The controller 22 then sends the room status to the housekeeping unit 8 and the admitting unit 6 and controls a display 28 of the central monitoring station 4 to display the room status for each room on the display 28. The controller 22, in one embodiment, also controls a display 18 of the in-room unit 2 that is provided in each of the rooms. The in-room unit display 18, the housekeeping unit display 34, and/or the central monitoring station display 28 displays the current status of the room that it is located in as well as the status of the medical equipment associated with the room. In one embodiment, the central station 4 may change the status of a room or medical equipment as well as the colorimetric indicator, visual color, symbology, or the like associated with the tag of the room or medical equipment.

To enable user interfacing and the exchange of room status data, central monitoring station 4 also includes a user interface 30 or an input/output (I/O) portion for each room 30, such as a drop down menu. The user interface 30 allows the user to view and/or manipulate the data of each room displayed on the display, e.g. a touch screen display. Alternatively, the central monitoring station optionally incorporates a keypad, keyboard, touch sensitive screen, or other user input device (not shown) to enable user input. In one embodiment, the user interface 30 also allows the user to define specific statuses for specific rooms in the display 28 as well as manually assign individual piece of medical equipment a status. The user interface 30 also allows the user to assign a cleaning personal to specific rooms, send manual messages to hospital personal, adjust protocols, system maintenance, change protocols for the medical equipment, the room changes, etc.

An evaluation unit 32 evaluates the cleaning information from each in-room unit 2 and determines the status of each of the rooms. For example, the evaluation unit 32 checks the status, measurement, or the like received from each of the sensors 10 and input 24 corresponding to a room. A room is given a clean status if all of the sensors 10 or other inputs indicate that all the equipment and room are clean and disinfected. A dirty status is given to any room in which one or more sensors 10 that sense at least one piece of medical equipment or the room is dirty. The evaluation unit 32 may include a suitable programmed computer or processor, software applied by the processor, or the like.

In another embodiment, the processor or controller 22 determines whether a room in the hospital should be assigned an occupied or dirty status. In one embodiment, the controller 22 receives information from the admitting unit 6 which is then used to determine when medical equipment or a room is clean or dirty. The admitting unit determines where patients are going and what the priorities with respect to cleaning the room. The monitoring system can keep the housekeeping system updated with clean/dirty status. When a patient is moved to another room within the hospital, the controller 22 via one of the in-room sensors 10, medical equipment, or through the admitting unit 6 detects the use of the patient ID in another room location. In response to detecting the patient ID in a new location, the controller 22 assigns a dirty status to the previously occupied room. The controller 22 also assigns an occupied status to a room in which the patient ID is now detected or assigned. The patient ID is transmitted from a patient ID bracelet, tag, or the like directly to the in-room unit 8 when a patient is in or enters the room. In another embodiment, the controller 22 determines whether a particular piece of medical equipment needs to be cleaned from the clean/dirty tag on the equipment and the patient ID. Once a patient is assigned to or begins using a piece of equipment its tag indicates that the medical equipment is dirty. However, as long same patient ID, and only the same patient ID, is detected associated with the piece of medical equipment it status is occupied, i.e. the equipment is not reclassified and duty removed for cleaning. When a patient is disassociated with the piece of medical equipment the status is changed to dirty. In another embodiment, the controller can change the status of a piece of equipment to dirty after a patient ID has been associated with the piece of equipment for a predetermined time period, e.g., in accordance with a recommended cleaning schedule from the manufacturer. In another embodiment, the controller 22 determines which pieces of medical equipment are assigned or unassigned to a patient ID. In response to determining that a piece of medical equipment is assigned to a patient ID, the medical equipment's tag is changed to an occupied status. The tag belonging to medical equipment that is not assigned a patient ID is changed to a dirty status. In a further embodiment, medical equipment that is assigned a patient ID is changed from an occupied status to a dirty status in response the assignment of the medical equipment extending a predetermined period of time.

In a further embodiment, the controller 22 provides notification to cleaning personal when a room has been assigned a dirty status. The notification includes a visual notification on the display, text message, voice message, text page, SMS, email, audio alarm, or the like. For example, a display 34 in the housekeeping unit 8 indicates which rooms are waiting to be cleaned, which rooms are in the process of being cleaned, which rooms have been cleaned, and the like. The controller 22 can also prioritize the display 34 so that rooms with a patient waiting are cleaned first. Priority can also be based on the condition of patients waiting for a room. The housekeeping unit 8 can interface with a staffing database (not shown) to assign and message or alert appropriate housekeepers or cleaning personal to the dirty rooms.

The controller 22 also provides notification to the admitting unit or bed assigning station 6 that a specific room in the hospital has been assigned a clean status and is ready for a new patient. In one embodiment, a communication unit 36 provides notification to the proper personal when rooms have been assigned a clean or dirty status. The communication unit 36 may include a suitable programmed computer or processor 26, software applied by the processor 26, or the like. The admitting unit 6 includes a display 38 showing the status of rooms, patients waiting to move from a room in one portion of the facility to another portion, information on patients waiting for a room, and the like. The admitting 6 unit also includes an input 40 by which information on patients waiting for a room is input, room assignments are manually made, transfers requested, equipment is assigned or unassigned to each patient or room, and the like.

The controller 22 also includes processor 26, for example, a microprocessor which is configured to execute room monitoring software for performing the operations and, optionally, room monitoring software. Typically, room monitoring software will be stored in a memory 41 or a computer readable medium and be executed by the processor. Types of computer readable medium include memory 41 such as a hard disk drive, CD-ROM, DVD-ROM and the like. Other implementations of the processor 28 are also contemplated. Display controllers, Application Specific Integrated Circuits (ASICs), and microcontrollers are illustrative examples of other types of component which may be implemented to provide functions of the processor 26. Embodiments may be implemented using software for execution by the processor 26, hardware, or some combination thereof.

Figure 2:
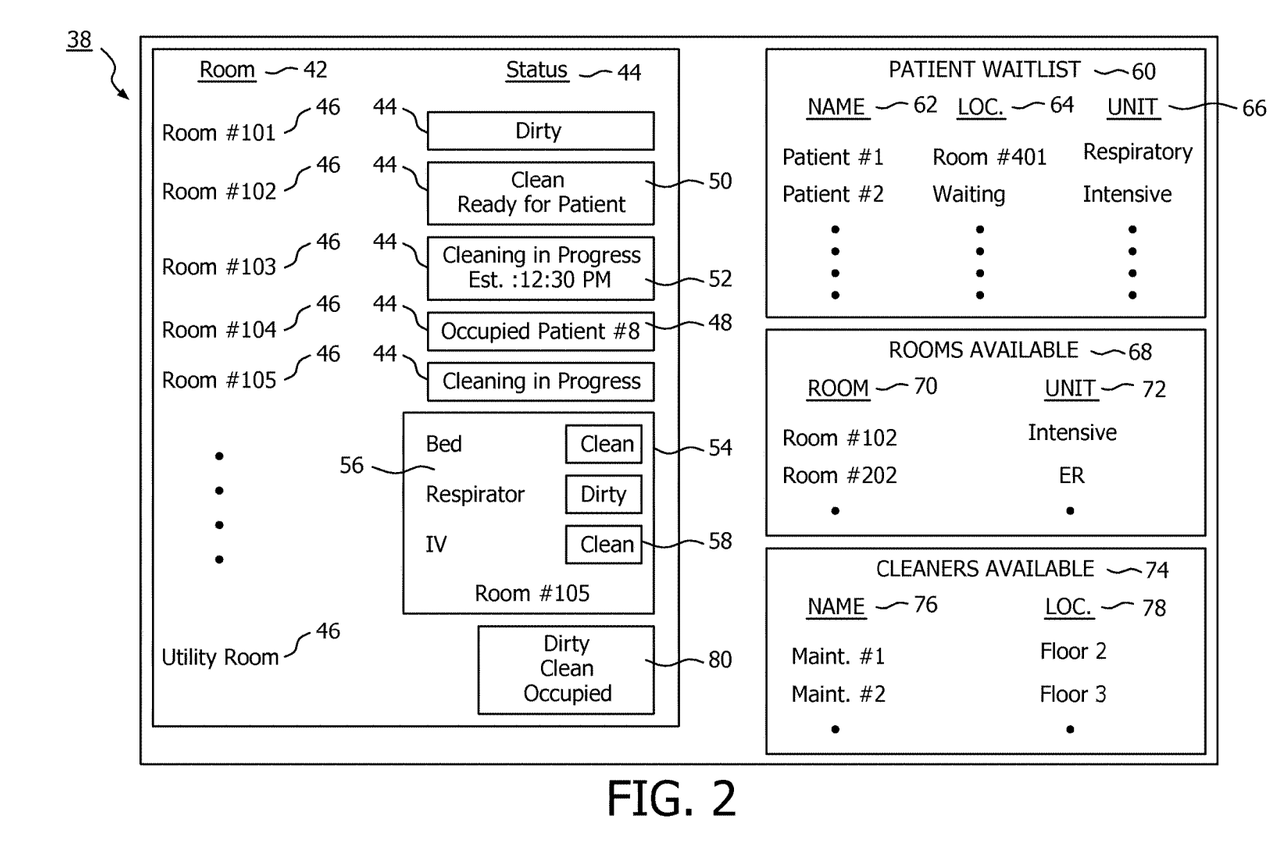
FIG. 2 illustrates an example of a central station interface.

As mentioned previously, the controller 22 directs one or more of the displays 28, 34, 38 to display the room status of various rooms determined from the cleaning information received from the various in-room units 2. With reference now to FIG. 2, in one embodiment the admitting unit display 38 of the bed assignment station displays a plurality of rooms 42 and the status 44 associated with each of those rooms 42. This or a similar display may also be provided in the central station 4. Five rooms 42 are illustrated in FIG. 2, but more or fewer rooms 42 are also contemplated as well as rooms other than patient room such as utility rooms and the like. The number of rooms 42 per bed assignment station could be dictated by the size of the display 38, the number of rooms 42, and other factors. As illustrated, the location 46 and status 44 of each room is displayed. The status bar 44 includes an indication of the status of the corresponding room 42. The status bars 44 may also include different color backgrounds or visually alerting aspects for each of the different statuses. For example, a dirty status may be displayed with a red background, a clean status may be displayed with a green background, a cleaning in progress may be displayed with a blue background, and an occupied status may be displayed with a white background. In another embodiment, a floor plan is displayed with each room displayed in a color indicative of its status.

In one embodiment, additional information is displayed along with the status 44. Rooms assigned an occupied status may display patient information associated with the room. Messages indicating that the room is ready for a new patient 50 may be displayed for rooms assigned a clean status. Rooms assigned a cleaning in progress status may include a time estimation 52 until the room is clean. The controller calculates the time estimation from the cleaning information and the cleaning protocol and determines when the medical equipment will approximately be cleaned. A look-up table of approximate cleaning times for each piece of medical equipment and cleaning chores or the like in memory 41, for example, is used to calculate the approximate time until all the room can be given a clean status. A real-time cleaning checklist 54 may also be displayed with any of the rooms. The cleaning information received from each piece of the medical equipment 56 associated with a room may be displayed such that cleaning personal knows the individual status 58 of each piece of medical equipment 56 in the room while they are cleaning. The checklist 54 may be placed as a pop-up with the display 38 or as an expanded window in the display 38.

In one embodiment, the bed assigning display 38 also includes a patient waiting list 60. The list may include the names or patient IDs 62, location 64, and appropriate unit 66 for patients that are waiting for an available room in a specific care unit specializing in the care for the patient type. In another embodiment, the bed assigning display 38 includes a list of rooms 68 that are currently available for new patients. The list of available rooms 68 may include the location 70 and the unit 72 of each of the rooms. In another embodiment, a list of available cleaning staff 74 may be displayed. In some cases only certain cleaners are capable of cleaning specific devices. This system can ensure the cleaner with the proper credentials is alerted to the suitable task to convert a dirty room to a clean room. The list of available cleaning staff 74 may include a list of personal available 76 to clean a room assigned a dirty status as well as their location 78 within the hospital. The list of available cleaning staff 74 as well as the room status may also be displayed on the display 34 of the housekeeping unit 8.

To enable user interfacing and the exchange of room status data, the bed assigning display 38 also includes a user interface 80 or an input/output (I/O) portion for each room 80, such as a touch sensitive drop down menu 80. The user interface 80 allows the user to view and/or manipulate the data of each room 42 displayed on the display 38, e.g. a touch screen display. Alternatively, the admitting unit optionally incorporates a keypad, keyboard, touch sensitive screen, or other user input device (not shown) to enable user input. In one embodiment, the user interface 80 also allows the user to define specific statuses 44 for specific rooms 42 in the display 38 as well as manually assign individual piece of medical equipment 56 a status. The user interface 80 also allows the user to assign a cleaning personal to specific rooms, send manual messages to hospital personal, adjust protocols, system maintenance, etc.

Figure 3:
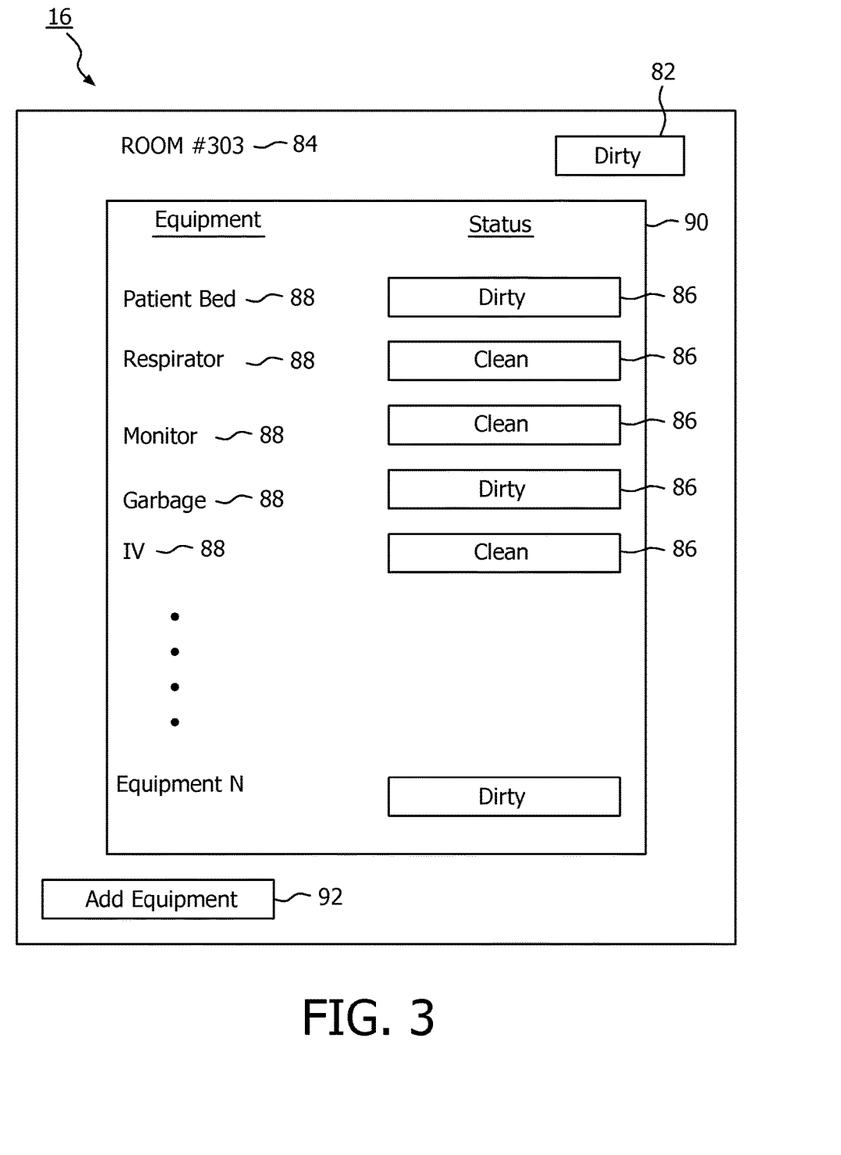
FIG. 3 illustrates an example of a display of the in-room unit.

FIG. 3 illustrates an example of the in-room display 18 of the in-room unit. The in-room display 18 displays the current overall status 82 of the room 84 as well as the status 86 of the medical equipment 88 associated with the room 84. The equipment associated with the room need not be in the room. For example, it may be at or in route to or from a sterilization or disinfections station. In one embodiment, the in-room display 18 displays the current overall status 82 of the room 84 as well as a cleaning checklist 90 that displays the current status 86 of the medical equipment 88 in the room to assist cleaning personal. To enable user interfacing and the exchange of room status data, in addition to the display, the in-room unit includes the user interface 18, 20 or an input/output (I/O) portion for each room 84. The room interface optionally incorporates a keypad, keyboard, touch sensitive screen, or other user input device 20 to enable user input. In one embodiment, the user interface 18, 20 also allows the user to define specific statuses 86 for specific medical equipment 88 associated with the room in the display 16 as well as the manual input of cleaning chores that are completed. The user interface 20 also allows the user to add new medical equipment or cleaning chores to room's checklist 90. In one embodiment, after a single use of disinfection equipment, the status of the equipment is changed to dirty. The central station causes a corresponding display on the housekeeping unit to call someone to remove the dirty equipment.

Figure 4:
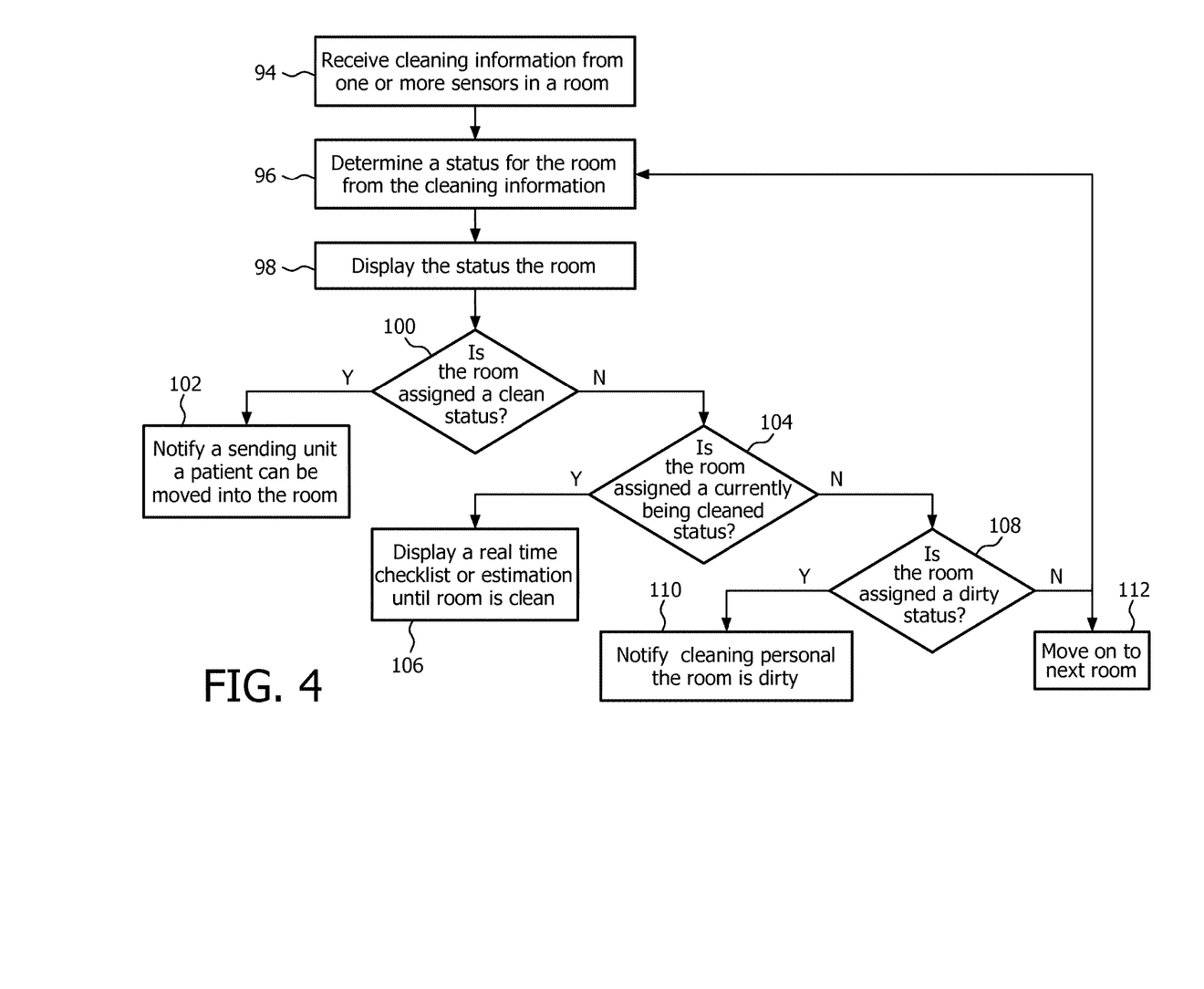
FIG. 4 is a flowchart diagram of the operation of the controller of the room monitoring system.

FIG. 4 illustrates the core operation of the controllers of the room monitoring system. In a step 94, the in-room unit receives cleaning information from one or more sensors locating in a room. In a step 96, the central monitoring station determines a status for the room based on the cleaning information received from the in-room unit. The room status is displayed in a display in a step 98. In a step 100, the central monitoring station determines whether the room is assigned a clean status. In response to the room having a clean status, the bed assigning unit is notified that a new patient can be moved into the room in a step 102. If the room is not assigned a clean status, the central monitoring station determines whether the room is assigned a currently being cleaned status in a step 104. In a step 106, a real time cleaning checklist or an estimation of the time until the room is clean is displayed in response to the room being assigned a currently being cleaned status. If the room is not assigned a currently being cleaned status, the central monitoring station determine whether the room is assigned a dirty status in a step 108. In response to the room having a dirty status, cleaning personal is notified that the room is dirty and ready for cleaning in a step 110. If the room is not assigned a dirty status, the room is currently being occupied. In response to the room being occupied, the central monitoring station continues to determine the status of the current room or moves on to determine the status of a next room in a step 112. The controllers are or include a processor which is programmed to perform the steps 94-112.

Figure 5:
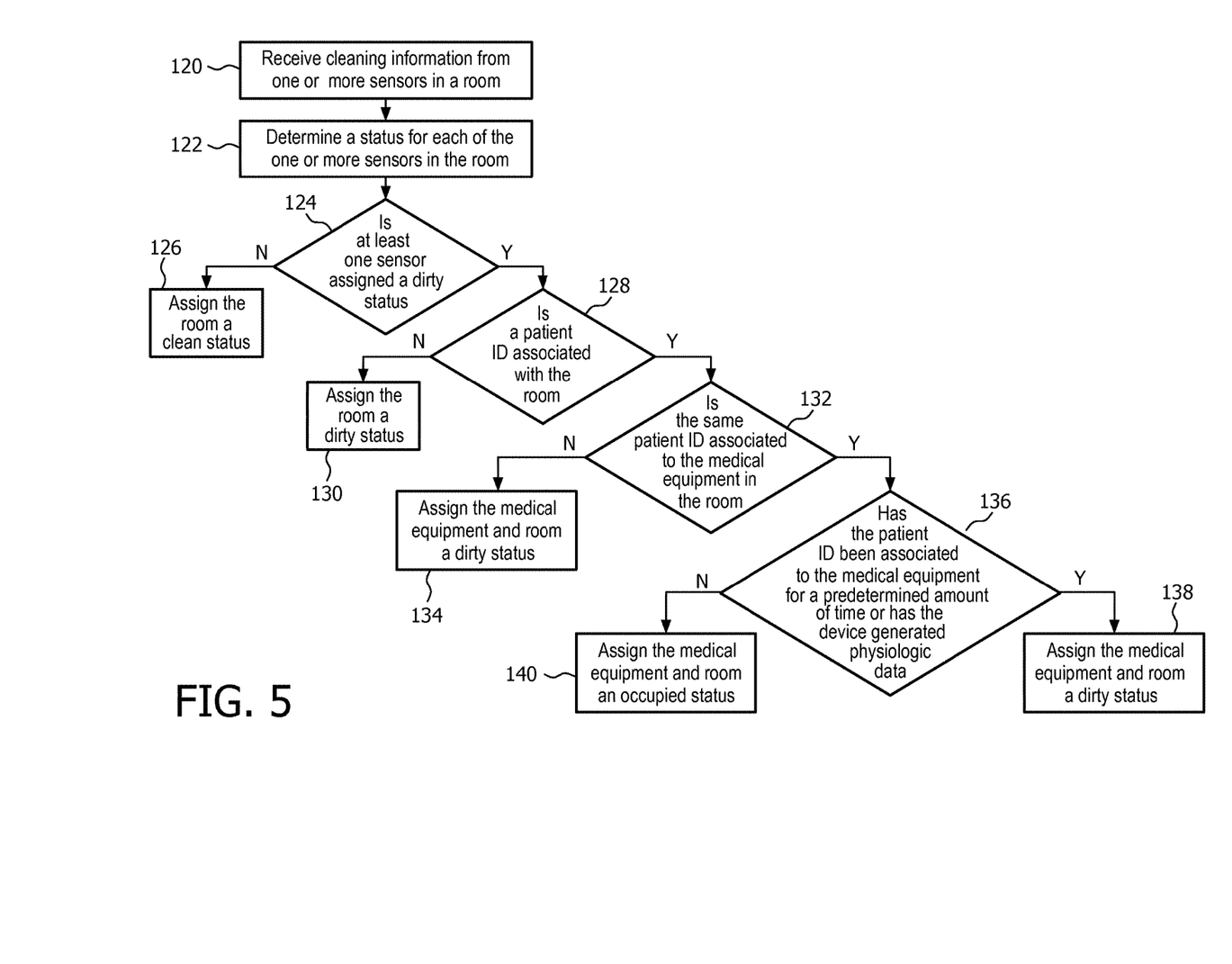
FIG. 5 is a flowchart diagram of the operation of the room monitoring system.

FIG. 5 illustrates operation of the room monitoring system. In a step 120, the in-room unit receives cleaning information from one or more sensors locating in a room. In a step 122, the central monitoring station or in-room unit determines a status for each of the one or more sensors in the room. The central monitoring station or in-room unit determines whether at least one sensor is assigned a dirty status in a step 124. In response to determining that none of the sensors are assigned a dirty status, the room is assigned a clean status in a step 126. In response to at least one of the sensors being assigned a dirty status, the central monitoring station or in-room unit determines whether a patient ID is associated with the room in a step 128. In a step 130, a dirty status is assigned if no patient ID is associated with the room. In response to a patient ID being associated with the room, the central monitoring station or in-room unit determines whether the same ID is associated with the medical equipment within the room in a step 132. In response to the patient ID associated with the room being the different from the patient ID associated with the medical equipment in the room, the medical equipment and room are assigned a dirty status in a step 134. In response to the patient ID associated with the room being the same as the patient ID associated with the medical equipment in the room, the central monitoring station or in-room unit determines whether the patient ID has been associated with the medical equipment for a predetermined amount of time or the device has generated physiologic data in a step 136. In a step 138, the medical equipment and room are assigned a dirty status if the patient ID is associated with the medical equipment for the predetermined amount of time. In response to the patient ID being associated with the medical equipment for less than the predetermined amount of time, the medical equipment and room are assigned an occupied or in use status in a step 140. The central monitoring station and the in-room units are or include a processor which is programmed to perform the steps 120-140.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A room monitoring system comprising:
a plurality of in-room units which collect information relating to a clean or dirty status of a plurality of patient rooms and/or equipment in the rooms, wherein the in-room units each include:
one or more sensors positioned in the room and configured to measure cleanliness of the patient room and/or equipment in the room;
wherein the sensors are configured to determine a presence of cleaning solution on surfaces of the patient rooms and/or the equipment in the patient rooms; and
a monitoring station which receives clean or dirty status information from the in-room units and determines which rooms are clean and ready for a patient, which are dirty and in need of cleaning, and which are occupied;
wherein the monitoring station is configured to determine whether the cleaning solution was sensed on the cleaning surfaces for an appropriate duration of time for disinfection.

2. The room monitoring system according to claim 1, further comprising:
a bed assigning unit which receives patient waiting information and room status information from the monitoring station and matches waiting patients with available clean rooms.

3. The room monitoring system according to claim 2, further comprising:
a housekeeping unit including a display which displays at least which rooms are waiting to be cleaned, which rooms are in a process of being cleaned, which rooms have been cleaned and a list of available cleaning personnel, the housekeeping unit being connected with the monitoring station to exchange information therewith.

4. The room monitoring system according to claim 1, wherein the in-room units each include:
a patient ID sensor which senses an ID of a patient in the room; and
a plurality of the sensors, each sensor sensing whether a piece of equipment in the room is clean or dirty;
wherein a controller of the monitoring system is configured to:
associate equipment with the patient in the room based on the sensed ID of the patient in the room,
classify each piece of the equipment in the room as in-use or dirty relative to patients not associated with the sensed patient ID,
classify the piece of equipment as dirty when the equipment is removed from the room, and
generate an alert in response to dirty equipment being brought into the room of another patient.

5. The room monitoring system according to claim 1, wherein the monitoring station is configured to issue an alert in response to attempting to move or assign a patient to a room determined to be dirty and/or in response to attempting to assign a patient to equipment determined to be dirty.

6. The room monitoring system according to claim 1, wherein the monitoring station includes:
a controller programmed to:
receive room status information from each of a plurality of the sensors in each of a plurality of the rooms;
determine the clean or dirty status for each of the rooms from the room status information received from the sensors in each of the rooms;
display the status of each of the rooms in a central display; and
notify cleaning personnel in response to determining one or more of the rooms have a dirty status.

7. The room monitoring system according to claim 1, wherein the in-room unit includes:
an ID sensor configured to sense an ID of a patient in the room;
a display configured to display clean or dirty status of the room or equipment in the room; and
a buffer memory configured to buffer communications between the room unit and the monitoring station.

8. The room monitoring system according to claim 1, wherein the monitoring station includes:
a controller with a processor programmed to:
control at least one of a in-room unit display, a monitoring station display, and a housekeeping unit display to display a checklist for each of the plurality of rooms, the checklist displaying a status of the patient room and a status of each piece of equipment in the room.

9. An in-room unit for use in the system of claim 1, comprising:
a display which displays the status of portions of the patient room and the equipment in the room; and
a controller which receives the clean or dirty status information from the one or more sensors and one of determines if the room is clean, and ready for a patient, is dirty and in need of cleaning, and is occupied, and transfers the information from the sensors to the monitoring station.

10. A method of displaying the status of medical rooms, the method comprising:
with sensors, sensing when a cleaning solution is on surfaces in the medical room,
with a computer, receiving signals from the sensors and determining the status of each of the medical rooms by determining whether the cleaning solution was sensed on the surfaces for an appropriate duration of time for disinfection;
with the computer, determining a clean or dirty status for each of the medical rooms from the determined room status;
displaying the status of each of the medical rooms in a display; and
generating a notification for cleaning personnel in response to determining one or more medical rooms has a dirty status.

11. The method according to claim 10, further including:
controlling at least one of a room display and central display to display a checklist for each of the medical rooms, the checklist displaying a status of each of the sensors in each of the medical rooms.

12. The method according to claim 10, further including:
determining whether mobile medical equipment in each of the rooms has left the room for sterilization/disinfection.

13. The method according to claim 10, further including:
notifying admitting personnel that a patient can be moved in response to determining one or more rooms having a clean status; and
displaying an estimation of a time remaining until a room is in a clean status or displaying a checklist for each of the one or more rooms, the checklist displaying a status of each of the sensors in each of the rooms for rooms having a cleaning in process status.

14. The method according to claim 10, further including:
in response to a patient ID becoming disassociated with a room, classifying the room and each piece of equipment in the room with the dirty status.

15. The method according to claim 10, further including:
in response to mobile equipment associated with a room or patient ID being sent to a cleaning unit, classifying the mobile equipment with the dirty status.

16. The room monitoring system according to claim 1, wherein the one or more sensors include:
a heterogeneous conductive patch mounted between two electrode plates to measure resistance, impedance, voltage, or current across the electrode plates; and
wherein the presence of the cleaning solution is determined by a sensing a change in the resistance or impedance of the matrix.

17. The method according to claim 10, wherein the one or more sensors include:
a heterogeneous conductive patch mounted between two electrode plates to measure resistance, impedance, voltage, or current across the electrode plates; and
further including:
sensing a change in the resistance or impedance across the plates over a period of exposure to the cleaning solution to detect the presence of the cleaning solution and a duration of time which the cleaning solution is present.

* * * * *